United States Patent
Giblin et al.

(10) Patent No.: US 6,924,297 B2
(45) Date of Patent: Aug. 2, 2005

(54) NAPHATHALENE DERIVATIVES WHICH BIND TO THE EP4 RECEPTOR

(75) Inventors: Gerard Martin Paul Giblin, Hertfordshire (GB); Haydn Terence Jones, Hertfordshire (GB); Andrew McMurtrie Mason, Hertfordshire (GB); Neil Derek Miller, Hertfordshire (GB); Susan Roomans, Hertfordshire (GB); Stephen Edward Shanahan, Hertfordshire (GB); Ann Louise Walker, Hertfordshire (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/450,891

(22) PCT Filed: Dec. 20, 2001

(86) PCT No.: PCT/GB01/05676

§ 371 (c)(1),
(2), (4) Date: Jan. 30, 2004

(87) PCT Pub. No.: WO02/50032

PCT Pub. Date: Jun. 27, 2002

(65) Prior Publication Data

US 2004/0102508 A1 May 27, 2004

(30) Foreign Application Priority Data

Dec. 21, 2000 (GB) .............................................. 0031302

(51) Int. Cl.⁷ ..................... A61K 31/403; C07D 209/60
(52) U.S. Cl. ...................... 514/339; 514/365; 514/364; 514/378; 514/411; 546/276.7; 548/450; 548/451; 548/181; 548/125; 548/247; 548/248

(58) Field of Search ................................ 548/450, 451, 548/181, 125, 247, 248; 546/276.7; 514/339, 365, 364, 378, 411

(56) References Cited

U.S. PATENT DOCUMENTS

| | | | |
|---|---|---|---|
| 4,014,899 A | 3/1977 | Bowman et al. | |
| 4,395,417 A | 7/1983 | Hall et al. | |
| 6,030,967 A | 2/2000 | Marui et al. | |

FOREIGN PATENT DOCUMENTS

| WO | WO 98/25899 | 6/1998 |
|---|---|---|
| WO | WO 00/76969 | 12/2000 |

*Primary Examiner*—Laura L. Stockton
(74) *Attorney, Agent, or Firm*—Grace C. Hsu; Mary E. McCarthy; Charles M. Kinzig

(57) ABSTRACT

Compounds of formula (I)

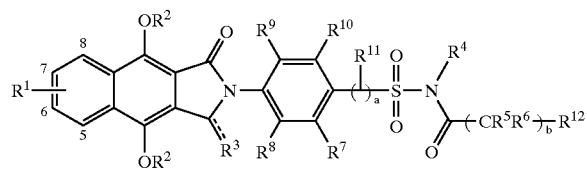

and pharmaceutically acceptable derivatives thereof bind with high affinity to the EP4 receptor and are of use in the treatment or prevention of conditions such as a pain, inflammatory, immunological, bone, neurodegenerative or renal disorder.

13 Claims, No Drawings

NAPHATHALENE DERIVATIVES WHICH BIND TO THE EP4 RECEPTOR

CROSS REFERENCES TO RELATED APPLICATIONS

This application is a National Stage Application filed under 35 U.S.C. §371 of PCT/GB01/05676, filed on Dec. 20, 2001, which claims priority of GB Application No. GB0031302.3, filed Dec. 21, 2000.

This invention relates to naphthalene derivatives, to processes for their preparation, to pharmaceutical compositions containing them and to their use in medicine.

The EP4 receptor is a 7-transmembrane receptor and its natural ligand is the prostaglandin $PGE_2$. $PGE_2$ also has affinity for the other EP receptors (types EP1, EP2 and EP3). The EP4 receptor is associated with smooth muscle relaxation, inflammation, lymphocyte differentiation, bone metabolism processes, allergic activities, promotion of sleep, renal regulation and gastric or enteric mucus secretion. We have now found a novel group of compounds which bind with high affinity to the EP4 receptor.

The invention thus provides compounds of the formula (I)

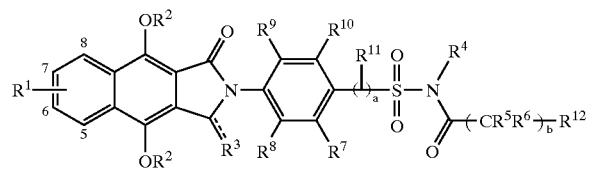

(I)

and pharmaceutically acceptable derivatives thereof in which:
a=0 or 1;
b=0 to 3;
$R^1$ is H, halogen, $C_{1-6}$alkyl, S—$C_{1-6}$alkyl, $C_{1-6}$alkoxy, $OCF_3$, $OCH_2CF_3$, O-cyclopropyl, $OCH_2$-cyclopropyl, $NH_2$, $NHC_{1-6}$alkyl, $N(C_{1-6}$alkyl$)_2$, $NO_2$, OH, $CH_2OC_{1-6}$alkyl or $CH_2OH$;
each $R^2$ is independently selected from $C_{1-4}$alkyl;
$R^3$ is H or O;
$R^4$ is H or $C_{1-6}$alkyl;
$R^5$ and $R^6$ are each independently selected from H, halogen, $C_{1-3}$alkyl, or are taken together to form a cyclopropyl ring;
$R^7$ to $R^{10}$ are each independently selected from H, $C_{1-6}$alkyl, $C_{1-6}$alkoxy, $C_{1-6}$alkoxy substituted by one or more fluorine atoms, O-cyclopropyl, $OCH_2$-cyclopropyl, S—$C_{1-6}$alkyl, $NH_2$, $NHC_{1-6}$alkyl, $N(C_{1-6}$alkyl$)_2$, halogen, $NO_2$, OH, $CH_2OC_{1-6}$alkyl, $CH_2OH$;
$R^{11}$ is selected from H, OH, halogen, dihalogen, $NH_2$, $NHC_{1-6}$alkyl, $N(C_{1-6}$alkyl$)_2$, $C_{1-6}$alkyl, $C_{1-6}$dialkyl, $C_{1-6}$alkoxy, $NHCO(C_{1-6}$alkyl$)$, or =O;
$R^{12}$ is selected from H, $C_{1-6}$alkyl, phenyl, phenyl substituted by one or more $R^{13}$, phenyl fused to a heterocycle, naphthyl, naphthyl substituted by one or more $R^{13}$, $C_{4-7}$cycloalkyl, $C_{4-7}$cycloalkyl fused to a benzene ring, $OCOC_{1-6}$alkyl, heteroaryl or heteroaryl substituted by one or more $R^{13}$;
$R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2H$, $CO_2C_{1-6}$alkyl, OH, $NH_2$, $NHC_{1-6}$alkyl, $N(C_{1-6}$alkyl$)_2$, $S(O)_nC_{1-6}$alkyl where n is 0, 1 or 2, $SO_2N(C_{1-6}$alkyl$)_2$, $CONH_2$, $CONHC_{1-6}$alkyl, $CON(C_{1-6}$alkyl$)_2$, $COC_{1-6}$alkyl, benzyloxy, $CH_2CO_2H$, $CH_2CO_2C_{1-6}$alkyl, $NO_2$ or $NHCO(C_{1-6}$alkyl$)$;
--- is a single bond or, when $R^3$ is O, a double bond.

By pharmaceutically acceptable derivative is meant any pharmaceutically acceptable salt or solvate of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be physiologically acceptable salts, but other salts may find use, for example in the preparation of compounds of formula (I) and the physiological acceptable salts thereof.

Pharmaceutically acceptable salts include those described by Berge, Bighley and Monkhouse, *J. Pharm. Sci.*, 1977, 66, 1–19. Suitable pharmaceutically acceptable salts include: acid addition salts formed with inorganic acids or organic acids, preferably inorganic acids e.g. hydrochlorides, hydrobromides, sulphates and acetates; and alkali metal salts, formed from the addition of alkali metal bases, such as alkali metal hydroxides e.g. sodium salts. Further representative examples of pharmaceutically acceptable salts include those formed from maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The term 'halogen' is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The term 'alkoxy' as a group or as part of a group means a straight or branched chain alkyl group having an oxygen atom attached to the chain, for example a methoxy, ethoxy, n-propoxy, i-propoxy, n-butoxy, s-butoxy or t-butoxy group.

The term 'heterocycle' as a group or as part of a group means a non-aromatic five or six membered ring which contains from 1 to 3 heteroatoms selected from nitrogen, oxygen or sulfur and which may be optionally substituted with one or more $C_{1-6}$alkyl groups. Examples of suitable heterocycles include 1,4-dioxane, 1,3-dioxolane and 2,2-dimethyl-1,3-dioxolane.

The term 'heteroaryl' as a group or as part of a group means a monocyclic five or six membered aromatic ring, or a fused bicyclic aromatic ring system comprising two of such monocyclic five or six membered aromatic rings. These heteroaryl rings contain one or more heteroatoms selected from nitrogen, oxygen or sulfur, where N-oxides, sulfur oxides and sulfur dioxides are permissible heteroatom substitutions. Examples of "heteroaryl" used herein include furan, thiophene, pyrrole, imidazole, pyrazole, triazole, tetrazole, thiazole, oxazole, isoxazole, oxadiazole, thiadiazole, isothiazole, pyridine, pyrimidine, quinoline, isoquinoline, benzofuran, benzothiophene, indole, and indazole.

In one aspect of the invention a=1.
In another aspect of the invention b=1.

In another aspect of the Invention $R^1$ is at the 6-position of the naphthalene ring, as defined in formula (I).

In another aspect of the invention $R^1$ is H or halogen.

In another aspect of the invention $R^1$ is H or bromine.

In another aspect of the invention each $R^2$ is ethyl.

In another aspect of the invention $R^4$ is H or methyl.

In another aspect of the invention $R^5$ and $R^6$ are each independently selected from H, chlorine, methyl or ethyl, or are taken together to form a cyclopropyl ring.

In another aspect of the invention each of $R^7$ to $R^{11}$ is hydrogen.

In another aspect of the invention $R^{12}$ is selected from $C_{1-6}$alkyl (preferably methyl), phenyl, phenyl substituted by one or more $R^{13}$, phenyl fused to a heterocycle selected from 1,4dioxane, 1,3-dioxolane and 2,2-dimethyl-1,3-dioxolane, naphthyl, naphthyl substituted by one or more $C_{1-6}$alkoxy (preferably methoxy), thiophene, thiazole, thiazole substituted by one or more $C_{1-6}$alkyl (preferably methyl), indole, indole substituted by one or more $C_{1-6}$alkyl (preferably methyl), or benzofuran.

In another aspect of the invention $R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2C_{1-6}$alkyl, OH, $N(C_{1-6}alkyl)_2$, $SO_2N(C_{1-6}alkyl)_2$, benzyloxy, $CH_2CO_2H$, $CH_2CO_2C_{1-6}$alkyl or $NO_2$.

In another aspect of the invention $R^{13}$ is chlorine, fluorine, methyl, ethyl, i-propyl, i-butyl, $CF_3$, methoxy, ethoxy, $OCF_3$, phenyl, CN, $CO_2CH_3$, OH, $NMe_2$, $SO_2NMe_2$, benzyloxy, $CH_2CO_2H$, $CH_2CO_2Me$ or $NO_2$.

In another aspect of the invention $R^{12}$ is phenyl substituted by one or two groups selected from chlorine (preferably as a substituent in the 2 or 4 position of the phenyl ring), fluorine (preferably as a substituent in the 2, 3, 4, or 2 and 5 positions of the phenyl ring), methyl (preferably as a substituent in the 2, 3 or 4 position of the phenyl ring, or, if two substituents are present, in the 2 and 5, or 2 and 6 positions of the phenyl ring), ethyl (preferably as a substituent in the 4 position of the phenyl ring), i-propyl (preferably as a substituent in the 4 position of the phenyl ring), i-butyl (preferably as a substituent in the 4 position of the phenyl ring), methoxy (preferably as a substituent in the 2, 3 or 4 position of the phenyl ring, or, if two substituents are present, in the 2 and 3, 3 and 4, 2 and 5, or 3 and 5 positions of the phenyl ring), ethoxy (preferably as a disubstituent in the 3 and 4 positions of the phenyl ring), $OCF_3$ (preferably as a substituent in the 3 or 4 position of the phenyl ring), phenyl (preferably as a substituent in the 4 position of the phenyl ring), benzyloxy (preferably as a substituent in the 3 position of the phenyl ring), or $CH_2CO_2Me$ (preferably as a substituent in the 2 position of the phenyl ring).

In another aspect of the invention $R^{12}$ is phenyl substituted by one or two groups selected from methyl (preferably substituted in the 4 position of the phenyl ring) or methoxy (preferably substituted in the 2, 3 or 4 position of the phenyl ring, or, if two substituents are present, in the 2 and 3 or 3 and 4 positions of the phenyl ring).

It is to be understood that the present invention covers all combinations of particular aspects of the invention as described hereinabove.

In a particular aspect of the invention there is provided a group of compounds of formula (I) (group A) wherein: a is 1, b is 1, $R^1$ is H or bromine; each $R^2$ is ethyl; $R^3$ is H; $R^4$ is H or methyl; $R^5$ and $R^6$ are each independently selected from H, halogen, $C_{1-3}$alkyl, or are taken together to form a cyclopropyl ring; each of $R^7$ to $R^{11}$ is hydrogen; $R^{12}$ is selected from H, $C_{1-6}$alkyl, phenyl, phenyl substituted by one or more $R^{13}$, phenyl fused to a heterocycle, naphthyl, naphthyl substituted by one or more $R^{13}$, $C_{4-7}$cycloalkyl, $C_{4-7}$cycloalkyl fused to a benzene ring, $OCOC_{1-6}$alkyl, heteroaryl or heteroaryl substituted by one or more $R^{13}$; $R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2H$, $CO_2C_{1-6}$alkyl, OH, $NH_2$, $NHC_{1-6}$alkyl, $N(C_{1-6}alkyl)_2$, $S(O)_nC_{1-6}$alkyl where n is 0, 1 or 2, $SO_2N(C_{1-6}alkyl)_2$, $CONH_2$, $CONHC_{1-6}$alkyl, $CON(C_{1-6}alkyl)_2$, $COC_{1-6}$alkyl, benzyloxy, $CH_2CO_2H$, $CH_2CO_2C_{1-6}$alkyl, $NO_2$ or $NHCO(C_{1-6}alkyl)$.

Within group A, there is provided a further group of compounds (group A1) wherein: $R^1$ is H; each $R^2$ is ethyl; $R^3$ is H; $R^4$ is H; $R^5$ and $R^6$ are each independently selected from H, chlorine, methyl or ethyl, or are taken together to form a cyclopropyl ring; each of $R^7$ to $R^{11}$ is hydrogen; $R^{12}$ is selected from phenyl, phenyl substituted by one or more $R^{13}$, phenyl fused to a heterocycle, naphthyl, naphthyl substituted by one or more $C_{1-6}$alkoxy, heteroaryl or heteroaryl substituted by one or more $C_{1-6}$alkyl; $R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2H$, $CO_2C_{1-6}$alkyl, OH, $NH_2$, $NHC_{1-6}$alkyl, $N(C_{1-6}alkyl)_2$, $S(O)_nC_{1-6}$alkyl where n is 0, 1 or 2, $SO_2N(C_{1-6}alkyl)_2$, $CONH_2$, $CONHC_{1-6}$alkyl, $CON(C_{1-6}alkyl)_2$, $COC_{1-6}$alkyl, benzyloxy, $CH_2CO_2H$, $CH_2CO_2C_{1-6}$alkyl, $NO_2$ or $NHCO(C_{1-6}alkyl)$.

Within group A there is provided a further group of compounds wherein $R^1$ is at the 6-position of the naphthalene ring, as defined in formula (I).

In a particular aspect of the invention there is provided a group of compounds of formula (I) (group B) wherein: a is 1, b is 1, $R^1$ is H or bromine; each $R^2$ is ethyl; $R^3$ is O; $R^4$ is H or methyl; $R^5$ and $R^6$ are each independently selected from H, halogen, $C_{1-3}$alkyl, or are taken together to form a cyclopropyl ring; each of $R^7$ to $R^{11}$ is hydrogen; $R^{12}$ is selected from H, $C_{1-6}$alkyl, phenyl, phenyl substituted by one or more $R^{13}$, phenyl fused to a heterocycle, naphthyl, naphthyl substituted by one or more $R^{13}$, $C_{4-7}$cycloalkyl, $C_{4-7}$cycloalkyl fused to a benzene ring, $OCOC_{1-6}$alkyl, heteroaryl or heteroaryl substituted by one or more $R^{13}$; $R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2H$, $CO_2C_{1-6}$alkyl, OH, $NH_2$, $NHC_{1-6}$alkyl, $N(C_{1-6}alkyl)_2$, $S(O)_nC_{1-6}$alkyl where n is 0, 1 or 2, $SO_2N(C_{1-6}alkyl)_2$, $CONH_2$, $CONHC_{1-6}$alkyl, $CON(C_{1-6}alkyl)_2$, $COC_{1-6}$alkyl, benzyloxy, $CH_2CO_2H$, $CH_2CO_2C_{1-6}$alkyl, $NO_2$ or $NHCO(C_{1-6}alkyl)$.

Within group B, there is provided a further group of compounds (group B1) wherein: $R^1$ is H; each $R^2$ is ethyl; $R^3$ is O; $R^4$ is H; $R^5$ and $R^6$ are each independently selected from H, chlorine, methyl or ethyl, or are taken together to form a cyclopropyl ring; each of $R^7$ to $R^{11}$ is hydrogen; $R^{12}$ is selected from phenyl, phenyl substituted by one or more $R^{13}$, phenyl fused to a heterocycle, naphthyl, naphthyl substituted by one or more $C_{1-6}$alkoxy, heteroaryl or heteroaryl substituted by one or more $C_{1-6}$alkyl; $R^{13}$ is halogen, $C_{1-6}$alkyl, $C_{1-6}$alkyl substituted by one or more fluorine atoms, $C_{1-6}$alkoxy, $C_{1-6}$alkoxy substituted by one or more fluorine atoms, phenyl, CN, $CO_2H$, $CO_2C_{1-6}$alkyl, OH, $NH_2$, $NHC_{1-6}$alkyl, $N(C_{1-6}alkyl)_2$, $S(O)_nC_{1-6}$alkyl where n is 0, 1 or 2, $SO_2N(C_{1-6}alkyl)_2$, $CONH_2$, $CONHC_{1-6}$alkyl, $CON(C_{1-6}alkyl)_2$, $COC_{1-6}$alkyl, benzyloxy, $CH_2CO_2H$, $CH_2CO_2C_{1-6}$alkyl, $NO_2$ or $NHCO(C_{1-6}alkyl)$.

Within group B there is provided a further group of compounds wherein $R^1$ is at the 6-position of the naphthalene ring, as defined in formula (I).

It is to be understood that the present invention encompasses all isomers of formula (I) and their pharmaceutically acceptable derivatives, including all geometric, tautomeric and optical forms, and mixtures thereof (e.g. racemic mixtures).

In one aspect the invention provides the following compounds and pharmaceutically acceptable derivatives thereof:

1-[4-(4,9-diethoxy-1-oxo-1,3-dihydro-2H-benzo[f]isoindol-2-yl)phenyl]-N-[(4-methoxyphenyl)acetyl]methanesulfonamide, 1-[4-(4,9-diethoxy-1-oxo-1,3-dihydro-2H-benzo[f]isoindol-2-yl)phenyl]-N-[(2-methoxyphenyl)acetyl]methanesulfonamide, 1-[4-(4,9-diethoxy-1-oxo-1,3-dihydro-2H-benzo[f]isoindol-2-yl)phenyl]-N-[(2,3-dimethoxyphenyl)acetyl]methanesulfonamide, 1-[4-(4,9-diethoxy-1-oxo-1,3-dihydro-2H-benzo[f]isoindol-2-yl)phenyl]-N-[(3,4-dimethoxyphenyl)acetyl]methanesulfonamide, 1-[4-(4,9-diethoxy-1-oxo-1,3-dihydro-2H-benzo[f]isoindol-2-yl)phenyl]-N-[(3-methoxyphenyl)acetyl]methanesulfonamide, 1-[4-(4,9-diethoxy-1,3-dioxo-1,3-dihydro-2H-benzo[f]isoindol-2-yl)phenyl]-N-[(3,4-dimethoxyphenyl)acetyl]methanesulfonamide, 1-[4-(4,9-diethoxy-1,3-dioxo-1,3-dihydro-2H-benzo[f]isoindol-2-yl)phenyl]-N-[(4-methylphenyl)acetyl]methanesulfonamide, and 1-[4-(4,9-diethoxy-1,3-dioxo-1,3-dihydro-2H-benzo[f]isoindol-2-yl)phenyl]-N-[(2-methoxyphenyl)acetyl]methanesulfonamide.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The compounds of the invention bind to the EP4 receptor and are therefore useful in treating EP4 receptor mediated diseases.

In view of their ability to bind to the EP4 receptor, the compounds of the invention are useful in the treatment of the disorders that follow. Thus, the compounds of formula (I) are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fanciers disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) are also useful in the treatment of immunological diseases such as autoimmune diseases, immunological deficiency diseases or organ transplantation. The compounds of formula (I) are also effective in increasing the latency of HIV infection.

The compounds of formula (I) are also useful in the treatment of diseases of abnormal platelet function (e.g. occlusive vascular diseases).

The compounds of formula (I) are also useful for the preparation of a drug with diuretic action.

The compounds of formula (I) are also useful in the treatment of impotence or erectile dysfunction.

The compounds of formula (I) are also useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of formula (I) may be useful in inhibiting bone resorption and/or promoting bone generation.

The compounds of formula (I) are also useful for attenuating the hemodynamic side effects of NSAIDs and COX-2 inhibitors.

The compounds of formula (I) are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also useful in the treatment of neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in preventing or reducing dependence on, or preventing or reducing tolerance or reverse tolerance to, a dependence—inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at EP4 receptors.

According to a further aspect of the invention, we provide a method of treating a human or animal subject suffering from a condition which is mediated by the action of $PGE_2$ at EP4 receptors which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by the action of $PGE_2$ at EP4 receptors.

According to another aspect of the invention we provide the use of a compound of formula (I) or a pharmaceutically acceptable derivative thereof for the manufacture of a therapeutic agent for the treatment or prevention of a condition such as a pain, inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The EP4 receptor compounds for use in the instant invention may be used in combination with other therapeutic agents, for example COX-2 inhibitors, such as celecoxib, rofecoxib, valdecoxib or parecoxib; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of compounds of formula (I) or their pharmaceutically acceptable salts for the treatment of man is from 0.01 to 10 mg/kg body weight per day and more particularly 0.1 to 3 mg/kg body weight per day, calculated as the free base, which may be administered as a single or divided dose, for example one to four times per day The dose range for adult human beings is generally from 8 to 1000 mg/day, such as from 20 to 800 mg/day, preferably 35 to 200 mg/day, calculated as the free base.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

Compounds of formula (I) and pharmaceutically acceptable derivatives thereof may be prepared by any method known in the art for the preparation of compounds of analogous structure.

Compounds of formula (I) and pharmaceutically acceptable derivatives thereof may be prepared by a process which comprises:
(A), coupling a sulfonamide of formula (II)

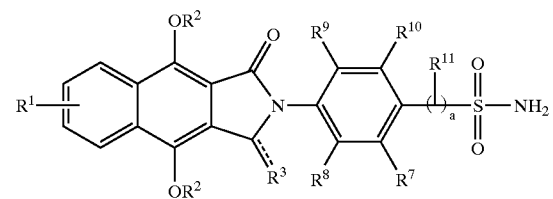

(II)

or a protected derivative thereof with an acid chloride of formula (III)

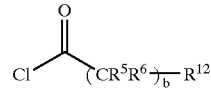

(III)

or a protected derivative thereof; or
(B), coupling a sulfonamide of formula (II)

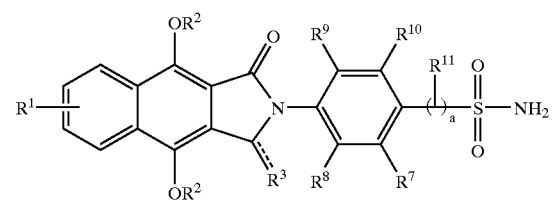

(II)

or a protected derivative thereof with an acid of formula (IV)

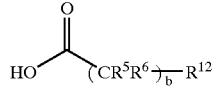

(IV)

or a protected derivative thereof; or
(C), interconversion of a compound of formula (I) into another compound of formula (I); or
(D), deprotecting a protected derivative of compound of formula (I); and
optionally converting compounds of formula (I) prepared by any one of the processes (A) to (D) into pharmaceutically acceptable derivatives thereof.

Suitable methods for the preparation of compounds of formula (I) and pharmaceutically acceptable derivatives thereof are described below, and form a further aspect of the invention. In the Schemes that follow, $R^1$ to $R^{12}$ are as defined in formula (I) above unless otherwise stated; DMF is dimethylformamide; DCM is dichloromethane; TFA is trifluoroacetic acid; DMAP is dimethylaminopyridine; Ac is acetyl; Hal is halogen.

Referring to Scheme 1 that follows, compounds of formula (I), wherein a is 1, $R^3$ is O and $R^4$ is H, may be prepared by coupling a compound of formula (II) with an acid chloride of formula (III) in the presence of a non-nucleophilic base, such as potassium carbonate or DMAP, in a suitable aprotic solvent such as acetone or toluene. In one embodiment of Scheme 1, potassium carbonate is added to a solution comprising a compound of formula (II) and an acid chloride of formula in acetone. The reaction mixture is then heated at about 80° C. under nitrogen for about 18 h. The reaction is then allowed to cool to ambient temperature and filtered to remove remaining solid. The filtrate is acidified using 2N hydrochloric acid and then diluted with water. The precipitate is then filtered off and triturated with diethylether to give a compound of formula (I), wherein a is 1, $R^3$ is O and $R^4$ is H, as a solid. In another embodiment of Scheme 1, DMAP is added to a solution comprising a compound of formula (II) and an acid chloride of formula (III) in toluene. The reaction mixture is then heated at about 120° C. under nitrogen for about 18 h. The reaction is then allowed to cool to ambient temperature and concentrated in vacuo. The residue is purified by chromatography eluting with ethyl acetate. The filtrate is then concentrated in vacuo and triturated with diethylether to give a compound of formula (I), wherein a is 1, $R^3$ is O and $R^4$ is H, as a solid.

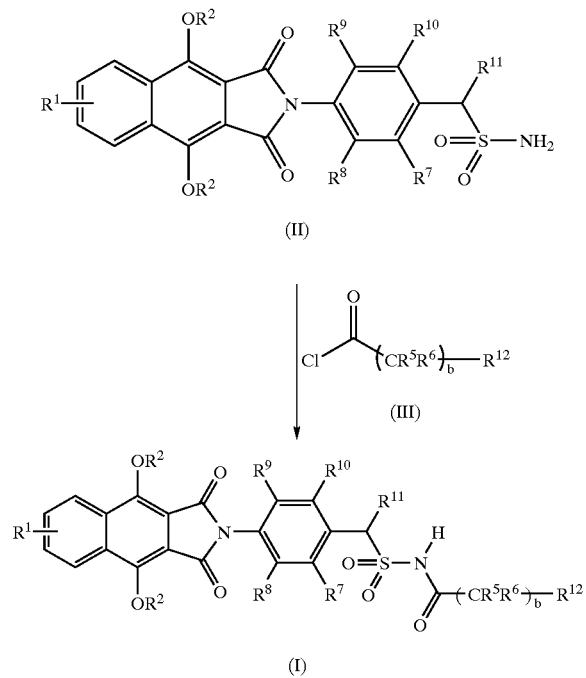

Referring to Scheme 2 that follows, compounds of formula (I), wherein a is 1, $R^3$ O and $R^4$ is H, may also be prepared by coupling a compound of formula (II) with an acid of formula (IV) in the presence of an activating agent, such as a carbodiimide, and a hindered organic amine base, such as DMAP, in a suitable aprotic solvent, such as DMF. Such couplings are described in many organic texts such as 'Principles of Peptide Synthesis' by Miklos Bodanszky (Springer Verlag, 1984) chapter 2, incorporated herein by reference. In one embodiment of Scheme 2, polymer supported carbodiimide (available from Argonaut Technologies, Inc.) is added to a solution comprising a compound of formula (II), DMAP and an acid of formula (IV) in DMF/DCM. The reaction mixture is then shaken at ambient temperature for about 18 h. The reaction mixture is then filtered and the resin is washed with DCM. The combined filtrate and washings are subject to an amino propyl SPE cartridge. Impurities are removed by elution with methanol and the desired product is removed by elution with methanol/acetic acid. The product filtrate is concentrated in vacuo and then triturated with methanol to give a compound of formula (I), wherein a is 1, $R^3$ is O and $R^4$ is H, as a solid.

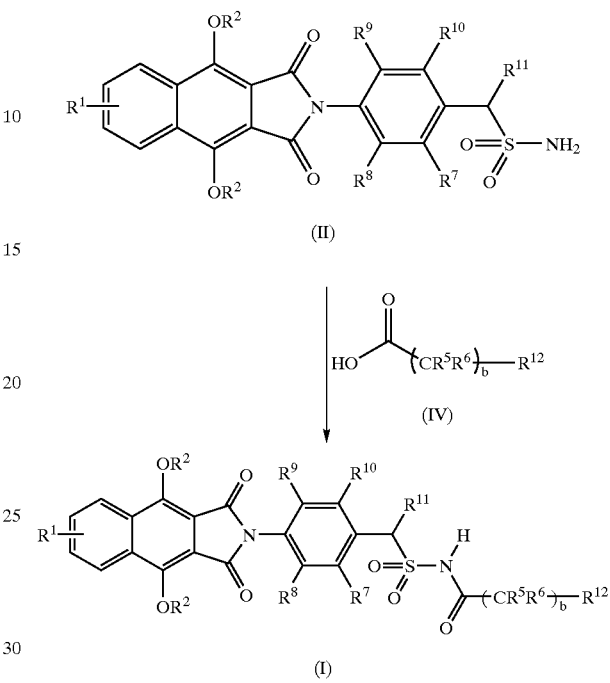

Compounds of formula (I) wherein $R^3$ is H may be synthesised in a manner analogous to Scheme 1 or 2. In this case, compounds of formula (II) are first converted to compounds corresponding to those of formula (II) wherein one of the C=O groups is converted to $CH_2$ via reduction with a suitable reducing agent. A suitable reducing agent is sodium borohydride in methanol followed by TFA and triethylsilane.

Acid chlorides of formula (III) and acids of formula (IV) are either known compounds or may be prepared by literature methods such as those described in 'Advanced Organic Chemistry' by Jerry March, fourth edition (John Wiley & Sons, 1992) page 1269 column 2, and page 1280 column 2, incorporated herein by reference.

It will be appreciated by those persons skilled in the art that compounds of formula (I) may be prepared by interconversion, utilising other compounds of formula (I) as precursors. In particular, alkylations are well known to those skilled in the art and are described in many standard organic chemistry texts such as 'Advanced Organic Chemistry'. For example, compounds of formula (I) wherein $R^4$ is $C_{1-6}$alkyl can be prepared by alkylating compounds of formula (I) wherein $R^4$ is H. Suitable alkylating agents include $C_{1-6}$alkyl iodides.

As will be appreciated by those skilled in the art, it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition (John Wiley and Sons, 1991), incorporated herein by reference, which also describes methods for the removal of such groups.

Compounds of formula (II) may, for example, be prepared according to Scheme 3 that follows.

Scheme 3

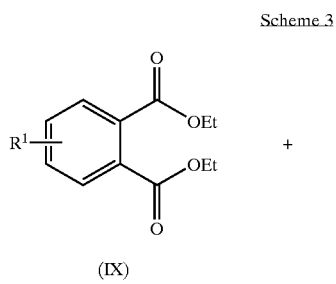

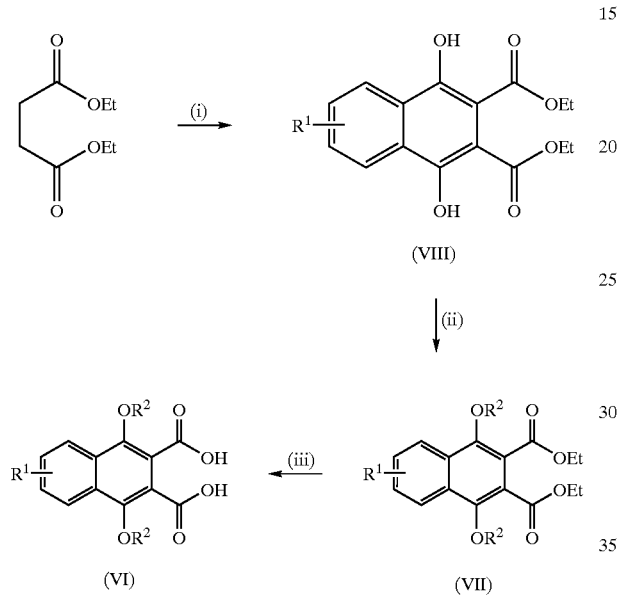

(i) Na, EtOH;
(ii) K₂CO₃, R²Hal, acetone;
(iii) NaOH, aq. EtOH;
(iv)

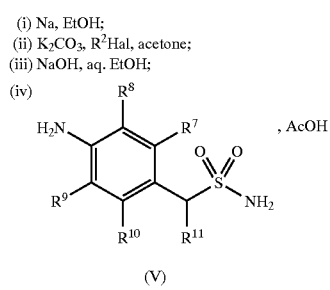

Compounds of formula (V) may, for example, be prepared according to Scheme 4 that follows.

Scheme 4

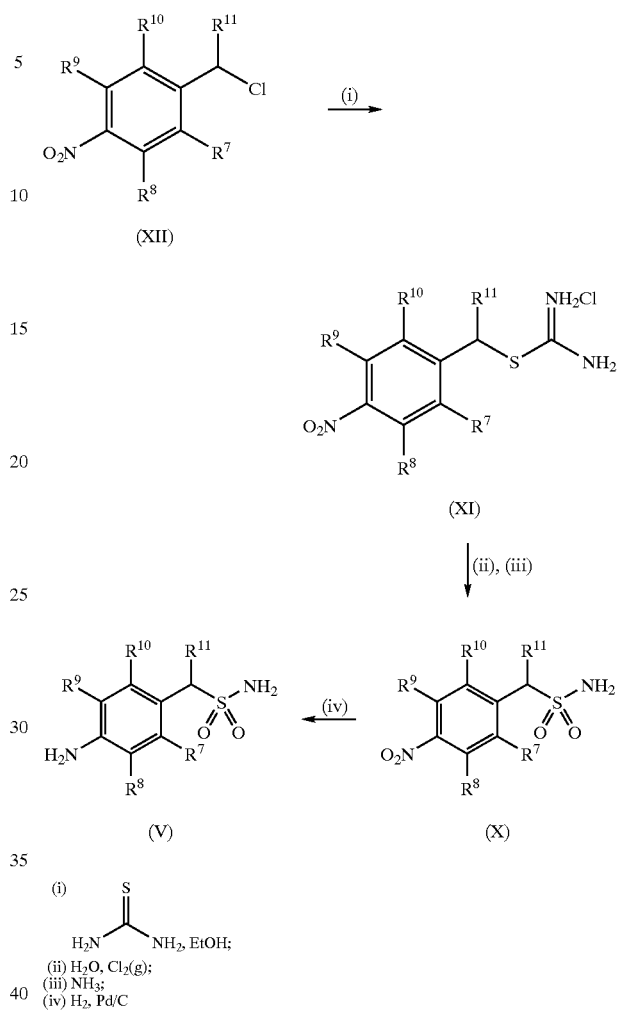

(i)

H₂N—C(=S)—NH₂, EtOH;
(ii) H₂O, Cl₂(g);
(iii) NH₃;
(iv) H₂, Pd/C

Phthalates of formula (IX) are either known compounds or may be prepared by conventional chemistry from commercially available starting materials.

4-Nitrobenzyl chlorides of formula (XII) are either known compounds or may be prepared by conventional chemistry from commercially available starting materials.

Compounds of formula (I) wherein a=0, may be synthesised in an analogous manner. In this case the compounds analogous to those of formula (V) but not possessing the CHR$^{11}$ moiety are commercially available thus rendering Scheme 4 unnecessary.

Certain intermediates described above are novel compounds, and it is to be understood that all novel intermediates herein form further aspects of the present invention.

Solvates (e.g. hydrates) or salts of a compound of the invention may be formed during the work-up procedure of any one of the aforementioned process steps.

The Intermediates and Examples that follow illustrate the invention but do not limit the invention in any way. All temperatures are in ° C. ¹H nmr spectra were obtained at 400 MHz on a Bruker DPX400. Mass directed autopurification was performed using a system comprising a HP1100 HPLC, a Gilson Aspec Autosampler, a HP1050 Make up Pump, a Micromass Platform Mass Spectrometer, a LC Packings Prep Accurate Combi-Chem Flow Processor (ACM-01-10), a Supelco 5 um ABZ+5 cm×10 mm ID Column and a Gilson Fraction Collector. The samples were dissolved in 50:50 acetonitrile:dimethylsulfoxide. A suitable gradient elution determined on the basis of the retention time of the compound in LC/MS was employed, for example 20–50% acetonitrile or 30–60% acetonitrile in water. The determination of such gradient elutions will be appreciated by those skilled in the art.

INTERMEDIATE 1

Ethyl 1,4-dihydroxy-2,3-naphthalenedicarboxylate

Sodium (60 g, 2.6 mol) was dissolved in ethanol (1.21) and the mixture was cooled to 40° C. Diethylphthalate (960 ml, 4.83 mol) was added and the mixture heated under nitrogen until the temperature reached 115° C. Diethyl succinate (211.3 g, 1.21 mol) was added dropwise over 45 min. The reaction was heated at 115° C. for a further 45 min, cooled to room temperature and poured onto water (1.2 l). Ethyl acetate (1 l) was added and stirred, the layers were separated and the organics were extracted with sodium hydroxide solution (2N, 1 l). The combined aqueous was acidified to pH 3 and the mixture extracted with ethyl acetate (2×1 l). The combined organics were washed with a saturated solution of sodium hydrogen carbonate (2×1.5 l), then brine, dried (MgSO$_4$), filtered and the solvent evaporated under vacuum. The residue was purified using a 2.5 kg Biotage column eluting with 5% ethyl acetate/hexane to give the title compound as a white solid, (60 g, 16%). δH CDCl$_3$ 10.44,(2H, s), 8.34,(2H, m), 7.68,(2H, m), 4.37,(4H, q), 1.37,(6H, t).

INTERMEDIATE 2

Ethyl 1,4-diethoxy-2,3-naphthalenedicarboxylate

Ethyl 1,4-dihydroxy-2,3-naphthalenedicarboxylate (30 g, 98.6 mmol) and potassium carbonate (150 g, 1.09 mmol) were stirred in acetone (600 ml) under nitrogen. Iodoethane (150 g, 0.96 mol) was added and the mixture was stirred at reflux overnight. The reaction was cooled, diluted with ethyl acetate and filtered. The filtrate was evaporated to leave a brown oil, which was dissolved in toluene and washed with potassium hydroxide solution (5%, 150 ml) and brine. Drying over magnesium sulphate and evaporation of the solvent gave a yellow solid. Purification using an 800 g Biotage column gave the title compound as a white solid (32 g, 90%). δH CDCl$_3$ 8.16,(2H, m), 7.60,(2H, m), 4.40,(4H, q), 4.18,(4H, q), 1.50,(6H, t), 1.40,(6H, t).

INTERMEDIATE 3

1,4-Diethoxy-2,3-naphthalenedicarboxylic acid

Ethyl 1,4diethoxy-2,3-naphthalenedicarboxylate (32 g, 89 mmol) was added to a solution of sodium hydroxide (20 g) in ethanol (200 ml) and water (40 ml) and stirred for 1.5 h at 60° C. The reaction was cooled and the thick white suspension was filtered. The solid was dissolved in a mixture of ethyl acetate (200 ml) and water (800 ml). The layers were separated and the aqueous was acidified with hydrochloric acid (2M, 120 ml). The aqueous was extracted with ethyl acetate (2×) and the combined organics were dried (MgSO$_4$). Evaporation of the solvent under vacuum gave the title compound as a white solid (25 g, 92%). δH [$^2$H$_6$]—DMSO 13.26,(2H, s), 8.15,(2H, m), 7.72,(2H, m), 4.13,(4H, q), 1.42,(6H, t).

INTERMEDIATE 4

4-nitrobenzyl imidothiocarbamate hydrochloride

A mixture of 4-nitrobenzylchloride (Aldrich, 85.8 g, 0.5 mol) and thiourea (Aldrich, 38.1 g, 0.5 mol) in ethanol (250 ml) was heated to reflux, under nitrogen, for 2.5 h. The reaction mixture was allowed to cool to ambient temperature and the precipitate was filtered off. The solid was washed with ethanol and diethylether and then dried in vacuo to give the title compound as a white solid (112.4 g, 90.8%). δH [$^2$H$_6$]—DMSO 4.72 (2H, s); 7.74 (2H, d, 9.4 Hz); 8.25 (2H, d, 9.4 Hz); 9.41 (3H, bds).

INTERMEDIATE 5

4-Nitro-benzylsulfonamide

Through a solution of Intermediate 4 (112.4 g, 0.45 mol) in water (2400 ml) was bubbled chlorine gas for 6 h at <12° C. The reaction mixture was extracted with ethyl acetate (×2) and the combined organic phases washed with water and brine. The precipitate, which formed on standing, was filtered off and discarded. The filtrate was concentrated in vacuo to give a oily yellow solid (70 g). This solid was added portionwise, with cooling, to 0.880 ammonia (450 ml). The mixture was stirred at ambient temperature for 1.5 h and then diluted with water (750 ml). The resultant precipitate was filtered off, washed with water and dried in vacua to give a pale yellow solid (25.5 g). This was heated in acetonitrle and filtered whilst hot. The filtrate was concentrated in vacuo and dried to give the title compound as a white solid (17.53 g, 18%). δH [$^2$H6]—DMSO 4.48 (2H, s); 6.99 (2H, s); 7.66 (2H, d, 9.5 Hz); 8.23 (2H, d, 9.5 Hz).

INTERMEDIATE 6

4-Amino-benzylsulfonamide

To 10% palladium on charcoal catalyst (3 g, 50% wet with water) under a nitrogen atmosphere was added a solution of 4-nitro-benzylsulfonamide (17.53 g, 81.1 mmol). in dimethylformamide (175 ml). The atmosphere of nitrogen was replaced with hydrogen and the mixture stirred vigourously for 5 h. The atmosphere was replaced with nitrogen and the mixture filtered through celite. The solvent was removed in vacuo and the residue triturated with diethylether to give a dark brown solid (14.7 g). The solid was heated in acetonitrile (440 ml) and filtered whilst hot (to remove excess catalyst). The filtrate was allowed to cool and the precipitate filtered off and dried in vacuo to give the title compound as a beige solid (12.32 g, 82%). δH [$^2$H$_6$]—DMSO 4.05 (2H, s); 5.11 (2H, s); 6.53 (2H, d, 8.2 Hz); 6.63 (2H, s); 7.01 (2H,d, 8.2 Hz).

INTERMEDIATE 7

1-[4-(4,9-diethoxy-1,3-dioxo-1,3-dihydro-2H-benzo[f]isoindol-2-yl)phenyl]methanesulfonamide To a solution of 1,4-diethoxy-2,3-naphthalenedicarboxylic acid (0.75 g, 2.5 mmol, 1.1 eqs) in glacial acetic acid (5 ml) was added 4-amino-benzylsulfonamide (0.43 g, 2.3 mmol). The reaction mixture was heated at 120° C. for 18 h. The reaction mixture was allowed to cool to ambient temperature and then poured into water (5 ml). The precipitate was filtered off, triturated with ethyl acetate/40:60 petroleum ether and then dried in vacuo to give the title compound as a beige solid (790 mg, 69%). δH [$^2$H$_6$]—DMSO 1.48 (6H, t); 4.40 (2H, s); 4.52 (4H, q); 7.00 (2H, s); 7.51 (2H, d, 8.5Hz); 7.56 (2H, d, 8.5 Hz); 7.89 (2H, m); 8.43 (2H, m)

INTERMEDIATE 8

1-[4-(4,9-diethoxy-1-oxo-1,3-dihydro-2H-benzo[f]isoindol-2-yl)phenyl]methanesulfonamide Sodium borohydride (0.5M solution in 2-methoxy ethyl ether, 56 ml, 23 mmol, 3.5 eqs) was added portionwise over 2 h to a suspension of Intermediate 7 (3 g, 6.6 mmol) in anhydrous methanol (60 ml) keeping the temperature below 0° C. The reaction mixture was stirred under nitrogen at 0° C. for a further 0.5 h. The reaction was quenched with saturated ammonium chloride solution (50 ml) and extracted with ethylacetate (×3). The combined organic extracts were dried (Na$_2$SO$_4$) and then concentrated in vacuo to give a pale yellow solid/oil. The solid/oil was added portionwise to trifluoroacetic acid (15 ml) at 0° C. Triethylsilane (1.48 ml, 9.3 mmol, 1.4 eqs) was added and stirring continued at 0° C.

for 10 mins. The temperature was allowed to reach ambient and stirring continued for a further 10 mins. The reaction mixture was concentrated in vacuo and the residue triturated with diethylether to give the title compound as a pink solid (2.3 g, 79%). δH [$^2$H$_6$]—DMSO 1.44 (3H, t); 1.50 (3H, t); 4.27 (2H, m); 4.30 (2H, q); 4.38 (2H, q); 5.18 (2H, s); 6.85 (2H, s); 7.43 (2H, d, 9 Hz); 7.57–7.75 (2,m); 8.01 (1H, d, 9 Hz); 8.32 (1H, d, 9 Hz);

EXAMPLE 1

1-[4-(4,9-diethoxy-1,3-dioxo-1,3-dihydro-2H-benzo[f]isoindol-2-yl)phenyl]-N-(phenylacetyl)methanesulfonamide To a solution of Intermediate 7 (40 mg, 0.088 mmol) and phenylacetyl chloride (77 mg, 0.5 mmol, 5.7eqs) in acetone (3.5 ml) was added potassium carbonate (100 mg, 0.72 mmol, 8.2 eqs). The reaction mixture was heated at 80° C. under nitrogen for 18 h. The reaction was allowed to cool to ambient temperature and then filtered to remove remaining solid. The filtrate was acidified using 2N hydrochloric acid and then diluted with water. The precipitate was filtered off and then triturated with diethylether to give the title compound as a beige solid (22 mgs, 43%). MH$^+$ 573.

The examples of Table 1 were prepared in the manner described for Example 1.

EXAMPLE 18

1-[4-(4,9-diethoxy-1-oxo-1,3-dihydro-2H-benzo[f]isoindol-2-yl)phenyl]-N-(phenylacetyl)methanesulfonamide To a solution of Intermediate 8 (176 mg, 0.4 mmol)) and phenylacetyl chloride (210 mg, 1.36 mmol, 3.4 eqs) in toluene (16 ml) was added 4-dimethylaminopyridine (100 mg, 0.8 mmol, 2 eqs). The reaction mixture was heated at 120° C. under nitrogen for 18 h. The reaction was allowed to cool to ambient temperature and then concentrated in vacuo. The residue was purified on a silica gel SPE cartridge eluting with ethylacetate. The filtrate was concentrated in vacuo and then triturated with diethylether to give the title compound as a cream solid (130 mg, 57.5%). MH$^+$ 559.

The examples of Table 2 were prepared in the manner described for Example 18.

TABLE 1

| Ex | a | b | R$^1$ | R$^3$ | R$^5$ | R$^6$ | R$^{12}$ | MH$^+$ |
|---|---|---|---|---|---|---|---|---|
| 2 | 1 | 1 | H | O | H | H | 4-methoxyphenyl | 603 |
| 3 | 1 | 0 | H | O | — | — | 4-cyanophenyl | 584 |
| 4 | 1 | 0 | H | O | — | — | phenyl | 559 |
| 5 | 1 | 0 | H | O | — | — | 3-fluorophenyl | 577 |
| 6 | 1 | 0 | H | O | — | — | 4-nitrophenyl | 604 |
| 7 | 1 | 0 | H | O | — | — | 4-fluorophenyl | 577 |
| 8 | 1 | 0 | H | O | — | — | methyl | 497 |
| 9 | 1 | 0 | H | O | — | — | n-butyl | 539 |
| 10 | 1 | 0 | H | O | — | — | t-butyl | 539 |
| 11 | 1 | 0 | H | O | — | — | cyclohexyl | 565 |
| 12 | 1 | 1 | H | O | H | H | OC(O)CH$_3$ | 555 |
| 13 | 1 | 0 | H | O | — | — | napth-2-yl | 609 |
| 14 | 1 | 0 | H | O | — | — | 5-methyl-1,2-oxazol-5-yl | 564 |
| 15 | 1 | 2 | H | O | H | H | phenyl | 587 |
| 16 | 1 | 2 | H | O | H | H | cyclohexyl | 593 |
| 17 | 1 | 0 | H | O | — | — | furan-2-yl | 549 |

TABLE 2

[Structure: naphthalene-fused isoindoline-1,3-dione with OEt groups at 4,9 positions, R¹ on naphthalene ring, N-aryl-(CH₂)ₐ-SO₂-NH-C(O)-(CR⁵R⁶)ᵦ-R¹²]

| Ex | a | b | R¹ | R³ | R⁵ | R⁶ | R¹² | MH⁺ |
|---|---|---|---|---|---|---|---|---|
| 19 | 1 | 1 | H | H | H | H | 3,4-dichlorophenyl | 627 |
| 20 | 1 | 1 | H | H | H | H | 4-methylphenyl | 573 |
| 21 | 1 | 1 | H | H | H | H | 2-methylphenyl | 573 |
| 22 | 1 | 1 | H | H | Me | Me | phenyl | 587 |
| 23 | 1 | 1 | H | H | H | H | 4-i-butylphenyl | 615 |
| 24 | 1 | 1 | H | H | H | H | 4-methoxyphenyl | 617 |
| 25 | 1 | 1 | H | H | H | H | 3-fluorophenyl | 577 |
| 26 | 1 | 1 | H | H | H | H | 3-methylphenyl | 573 |
| 27 | 1 | 1 | H | H | H | H | 4-i-propylphenyl | 601 |
| 28 | 1 | 1 | H | H | H | H | 4-ethylphenyl | 587 |
| 29 | 1 | 1 | H | H | H | H | 2-chlorophenyl | 593 |
| 30 | 1 | 1 | H | H | H | H | 4-phenylphenyl | 635 |
| 31 | 1 | 1 | H | H | H | H | 2-methoxyphenyl | 589 |
| 32 | 1 | 1 | H | H | H | H | 2-fluorophenyl | 577 |
| 33 | 1 | 1 | H | H | H | H | 4-trifluoromethylphenyl | 627 |
| 34 | 1 | 1 | H | H | H | H | 2,3-dimethoxyphenyl | 619 |
| 35 | 1 | 1 | H | H | H | H | 4-hydroxyphenyl | 575 |
| 36 | 1 | 1 | H | H | H | H | 2,5-dimethoxyphenyl | 619 |
| 37 | 1 | 1 | H | H | H | H | 4-dimethylaminophenyl | 602 |
| 38 | 1 | 1 | H | H | H | H | 3,4-dimethoxyphenyl | 619 |
| 39 | 1 | 1 | H | H | H | H | 2,5-dimethylphenyl | 587 |
| 40 | 1 | 1 | H | H | Me | H | 4-i-butylphenyl | 629 |
| 41 | 1 | 1 | H | H | H | H | 2-benzyloxyphenyl | 665 |
| 42 | 1 | 1 | H | H | H | H | 3-benzyloxyphenyl | 665 |
| 43 | 1 | 1 | H | H | H | H | 3-methoxyphenyl | 589 |
| 44 | 1 | 1 | H | H | H | H | 2-(CH₂CO₂H)phenyl | 617 |
| 45 | 1 | 1 | H | H | H | H | 4-(CO₂Me)phenyl | 617 |
| 46 | 1 | 1 | H | H | H | H | 4-(SO₂NMe₂)phenyl | 666 |
| 47 | 1 | 1 | H | H | H | H | 2-(CH₂CO₂Me)phenyl | 631 |
| 48 | 1 | 1 | H | H | H | H | naphth-2-yl | 609 |
| 49 | 1 | 0 | H | H | — | — | [bicyclo[4.2.0]octa-1,3,5-trien-7-ylmethyl] | 571 |
| 50 | 1 | 1 | H | H | cyclopropyl | | phenyl | 585 |
| 51 | 1 | 1 | H | H | H | H | thiophen-3-yl | 565 |
| 52 | 1 | 1 | H | H | H | H | pyridin-3-yl | 560 |
| 53 | 1 | 1 | H | H | H | H | thiophen-2-yl | 565 |
| 54 | 1 | 1 | H | H | H | H | pyridin-2-yl | 560 |
| 55 | 1 | 1 | H | H | H | H | pyridin-4-yl | 560 |
| 56 | 1 | 1 | H | H | H | H | 2-methyl-1,3-thiazol-4-yl | 580 |
| 57 | 1 | 1 | H | H | H | H | 4-methyl-1,2,5-oxadiazol-3-yl | 565 |
| 58 | 1 | 1 | H | H | H | H | 5-methyl-1,2-oxazol-3-yl | 564 |
| 59 | 1 | 1 | H | H | H | H | 3-methyl-1,2-oxazol-5-yl | 564 |
| 60 | 1 | 1 | H | H | H | H | 4-methyl-1,3-thiazol-5-yl | 580 |

The examples of Table 3 were prepared in the manner described for Example 18 except Intermediate 8 was replaced with intermediate 7.

TABLE 3

| Ex | a | b | R¹ | R³ | R⁵ | R⁶ | R¹² | MH⁺ |
|----|---|---|----|----|----|----|-----|-----|
| 61 | 1 | 1 | H | O | H | H | 2-methylphenyl | 587 |
| 62 | 1 | 1 | H | O | H | H | 4-fluorophenyl | 591 |
| 63 | 1 | 1 | H | O | H | H | 3-methoxyphenyl | 603 |
| 64 | 1 | 1 | H | O | Et | H | phenyl | 601 |
| 65 | 1 | 1 | H | O | H | H | 3-fluorophenyl | 591 |
| 66 | 1 | 1 | H | O | H | H | 3,4-dimethoxyphenyl | 633 |
| 67 | 1 | 1 | H | O | H | H | 4-methylphenyl | 587 |
| 68 | 1 | 1 | H | O | Me | H | phenyl | 587 |
| 69 | 1 | 1 | H | O | H | H | 2,5-difluorophenyl | 609 |
| 70 | 1 | 1 | H | O | H | H | 4-chlorophenyl | 607 |
| 71 | 1 | 1 | H | O | H | H | 2-methoxyphenyl | 603 |
| 72 | 1 | 1 | H | O | H | H | 2,6-dimethylphenyl | 601 |
| 73 | 1 | 1 | H | O | Me | Me | 3-methylphenyl | 615 |
| 74 | 1 | 1 | H | O | H | H | 3-fluoro-4-methylphenyl | 605 |
| 75 | 1 | 1 | H | O | Cl | H | phenyl | 607 |
| 76 | 1 | 1 | H | O | H | H | naphth-1-yl | 623 |
| 77 | 1 | 1 | H | O | H | H | naphth-2-yl | 623 |
| 78 | 0 | 0 | H | O | — | — | methyl | 555 |

EXAMPLE 79

1-[4-(4,9-diethoxy-1-oxo-1,3dihydro-2H-benzo[f]isoindol-2-yl)phenyl]-N-[(4-methyl-1,3-thiazol-5-yl)acetyl]methanesulfonamide To a solution of Intermediate 8 (44 mg, 0.1 mmol), 1-[4-methyl-1,3-thiazol-5-yl]acetic acid (32 mg, 0.2 mmol, 2 eqs) and 4-dimethylaminopyridine (74 mg, 0.6 mmol, 6 eqs) in dimethylformamide (2 ml) and dichloromethane (2 ml) was added polymer supported carbodiimide (Argonaut Technologies, Inc., 480 mg, 0.45 mmol, 4.5 eqs). The reaction mixture was shaken at ambient temperature for 18 h. The reaction was filtered and the resin washed with dichloromethane. The combined filtrate and washings were subject to an amino propyl SPE cartridge. Impurities were removed by elution with methanol and the required product was removed by elution with methanol/acetic acid. The product filtrate was concentrated in vacuo and then triturated with methanol to give the title compound as a beige solid. MH⁺ 580.

The examples of Table 4 were prepared in the manner described for Example 79.

TABLE 4

| Ex | a | b | R¹ | R³ | R⁵ | R⁶ | R¹² | MH⁺ |
|----|---|---|----|----|----|----|-----|-----|
| 80 | 1 | 1 | H | H | H | H | 4-trifluoromethoxyphenyl | 643 |
| 81 | 1 | 1 | H | H | H | H | 3-trifluoromethoxyphenyl | 643 |
| 82 | 1 | 1 | H | H | H | H | 3,4-diethoxyphenyl | 647 |
| 83 | 1 | 1 | H | H | H | H | 3,5-dimethoxyphenyl | 619 |
| 84 | 1 | 1 | H | H | H | H | 5-methyl-1,3-benzodioxol-yl | 603 |

TABLE 4-continued

| Ex | a | b | R¹ | R³ | R⁵ | R⁶ | R¹² | MH⁺ |
|----|---|---|----|----|----|----|-----|-----|
| 85 | 1 | 1 | H | H | H | H | (2,2-dimethyl-benzo[1,3]dioxol-5-yl) | 631 |
| 86 | 1 | 1 | H | H | Me | H | 6-methoxy-naphth-2-yl | 653 |
| 87 | 1 | 1 | H | H | H | H | (1-methyl-indol-2-yl) | 598 |
| 88 | 1 | 1 | H | H | H | H | (benzofuran-4-yl) | 599 |
| 89 | 1 | 1 | H | H | H | H | (1-methyl-indol-3-yl) | 612 |
| 90 | 1 | 1 | H | H | H | H | (benzofuran-2-yl) | 599 |
| 91 | 1 | 0 | H | H | — | — | (2,3-dihydro-benzo[1,4]dioxin-6-yl) | 603 |
| 92 | 1 | 0 | H | H | — | — | (1-methyl-indol-3-yl) | 626 |

The example of Table 5 was prepared in the manner described for Example 79 except Intermediate 8 was replaced with Intermediate 7.

TABLE 5

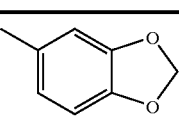

| Ex | a | b | R¹ | R³ | R⁵ | R⁶ | R¹² | MH⁺ |
|----|---|---|----|----|----|----|-----|-----|
| 93 | 1 | 1 | H  | O  | H  | H  | (1,3-benzodioxol-5-yl) | 617 |

EXAMPLE 94

1-[4-(4,9-diethoxy-1,3-dioxo-1,3-dihydro-2H-benzo[f]isoindol-2-yl)phenyl]-N-[(4-methoxyphenyl)acetyl]-N-methyl-methanesulfonamide To a solution of the product of Example 2 (40 mg, 0.066 mmol)) and methyl iodide (0.032 ml, 0.51 mmol, 7.7 eqs) in acetonitrile (5 ml) was added sodium carbonate (14 mg, 0.133 mmol, 2 eqs). The reaction mixture was stirred at ambient temperature under nitrogen for 18 h. The reaction was concentrated in vacuo and then partioned between ethylacetate (20 ml) and 2N hydrochloric acid (20 ml). The organic phase was washed with brine, dried (MgSO₄) and then concentrated in vacuo. The residue was preabsorbed onto silica and purified on a silica gel SPE cartridge eluting with an ethylacetate/petroleum ether gradient. The solvent was removed in vacuo to give the title compound as a yellow solid (15 mg, 36%). MH+ 617.

Biological Data

The ability of the compounds to bind to EP4 receptors may be demonstrated in the Human $EP_4$ Scintillation Proximity Assay.

Quantification of radioligand binding by scintillation proximity assay (SPA) is a long-established principle. Briefly, the affinity of compounds for a receptor is assessed by the specific competition between known quantities of radiolabelled ligand and compound for that receptor. Increasing concentrations of compound reduce the amount of radiolabel that binds to the receptor. This gives rise to a diminishing scintillation signal from SPA beads coated with membranes that bear the receptor. The signal may be detected with a suitable scintillation counter and the data generated may be analysed with suitable curve-fitting software.

The human $EP_4$ SPA assay (hereafter referred to as 'the assay') utilises membranes prepared from Chinese Hamster Ovary (CHO cells) infected with Semliki Forest Virus (SFV). Genetically engineered SFV-1 viral particles containing the genetic sequence of the human EP4 receptor were used to infect CHO cells resulting in expression of the receptor protein in cellular membranes. Cells washed free of media are homogenised in a pH-buffered medium containing peptidase inhibitors. A suitable buffer is of the following composition: 50 mM HEPES, 1 mM EDTA, 25 μg/ml bacitracin, 100 μM leupeptin, 1 mM PMSF, 2 μM Pepstatin A, pH adjusted to 7.4 with KOH. Following removal of cell debris by a low-speed centrifugation, a pellet of membranes is prepared by a high-speed (48000 g) centrifugation of the resulting supernatant. Membrane suspensions such as that described may be stored at −80° C. until used.

For assay, membranes expressing human $EP_4$ receptors are diluted in a pH-buffered medium and mixed with SPA beads coated with a suitable substance to facilitate the adhesion of membranes to the beads. The concentrations of membrane protein and SPA beads chosen should result in SPA binding signal of at least 300 corrected counts per minute (CCPM) when tritiated radioligand at a concentration close to its $K_d$ (affinity value) is combined with the mixture. Non-specific binding (nsb) may be determined by competition between the radiolabelled ligand and a saturating concentration of unlabelled ligand. In order to quantify the affinity of EP4 receptor ligands, compounds are diluted in a stepwise manner across the wells of a 96-well plate. Radioligand, compound, and unlabelled ligand are then added to a 96-well plate suitable for the measurement of SPA binding signals prior to the addition of bead/membrane mixture to initiate the binding reaction. Equilibrium may be achieved by incubation at room temperature for 120 minutes prior to scintillation counting. The data so generated may be analysed by means of a computerised curve-fitting routine in order to quantify the concentration of compound that displaces 50% of the specific radioligand binding ($IC_{50}$). The affinity ($pK_i$) of the compound may be calculated from the $IC_{50}$ by application of the Cheng-Prusoff correction. Suitable reagents and protocols are: reaction buffer containing 50 mM HEPES, 10 mM $MgCl_2$, pH adjusted to 7.4 with KOH; SPA beads coated with wheatgerm agglutinin; 1.25 nM [$^3$H]-prostaglandin $E_2$ as radioligand; 10 μM prostaglandin $E_2$ as unlabelled ligand; a three-fold dilution series of compound starting at 10 μM and ending at 0.3 nM is adequate.

The ability of the compounds to antagonise EP4 receptors may be demonstrated in the [$^{125}$I]cAMP Scintillation Proximity Assay (hereafter referred to as 'the cAMP assay'). The cAMP assay utilises HEK-293 cells expressing the recombinant human EP4 receptor, obtained from Receptor Biology, Inc. Beltsville, Md., USA. The cells are cultured in Dulbecco's Modified Eagle Medium—HAM F12 mix (DMEM-F12), containing 10% heat inactivated-foetal bovine serum (FBS) and 2 mM L-glutamine. The cells are either passaged into fresh medium or used in an assay once 90% confluency as determined visually had been achieved.

The cells are harvested by treatment with Versene, re-suspended in fresh culture medium and plated out to yield approximately 10,000 cells per well of a 96-well plate for overnight culture in culture medium additionally supplemented with 3 μM indomethacin. For assay, the culture medium is replaced with assay medium (DMEM-F12 containing 300 μM isobutylmethylxanthine (IBMX) and 3 μM indomethacin) and incubated for 30 minutes. Following this, antagonist is then added at various concentrations such that an entire agonist concentration-effect curve can be obtained in the presence of a single concentration of the antagonist. The antagonist is allowed to equilibrate with the cells for 30 minutes. Subsequently the cells are challenged with an agonist for 15 minutes. The reaction is stopped by the aspiration of the assay medium and the addition of ice-cold ethanol. All incubations are carried out at 37° C. in a 5% carbon dioxide atmosphere. Care must be taken to ensure the constancy of IBMX, indomethacin and vehicle (DMSO) concentrations throughout. The amount of cAMP in each well is then determined by [$^{125}$I]cAMP scintillation proximity assay using a proprietary kit, obtained from Amersham, Buckinghamshire, UK, and according to the manufacturer's instructions.

Data from cAMP assays are expressed as pmol cAMP per well. A four-parameter logistic equation of the form:

$$E=((Em.[A]\hat{}nH)/((EC_{50}\hat{}nH)+([A]\hat{}nH))$$

is then fitted to E/[A] curve data in order to estimate maximum effect (Em), curve mid-point (EC50), and Hill slope (nH); other terms in the equation are effect (E) and concentration ([A]). Individual estimates of curve parameters are obtained from each curve. An empirical estimate of antagonist affinity (pA$_2$) could then be obtained using the following formula:

$$pA_2=\log((EC_{50}^B/EC_{50}^A)-1)-\log[B]$$

where $EC_{50}^A$ is the midpoint of a control agonist concentration-effect curve in the absence of antagonist; $EC_{50}^B$ is the midpoint of an agonist concentration effect curve produced in the presence of a fixed concentration of antagonist; and [B] is the concentration of antagonist used. Estimates from individual experiments are then averaged to provide mean data. Quoted values are therefore the mean±standard deviation (s.d.) of n separate experiments, each derived from a separate cAMP assay.

For the rigorous estimation of antagonist affinity values (pK$_b$) the method of Arunlakshana and Schild is employed. Briefly, the midpoint of agonist concentration/effect curves in the presence and absence of antagonist are used to calculate concentration ratios (CR). Linear regression is performed on a plot of (CR-1) against concentration of antagonist (-log[B]) in order to estimate the point of intersection with the concentration (-log[B]) axis and the slope of the line. If the slope of the regression does not differ significantly from unity then it may be constrained to 1.0. Under this latter circumstance, the point of intersection on the concentration axis represents the affinity (pK$_b$) of the antagonist.

The following examples have a pK$_I$ of 7.0 or greater at EP4 receptors as determined using the above-mentioned procedure:
1, 2, 18, 20, 21, 22, 23, 24, 25, 26, 27, 28, 29, 30, 31, 32, 34, 36, 38, 39, 40, 42, 43, 47, 48, 50, 51, 60, 61, 62, 63, 64, 65, 66, 67., 68, 69, 70, 71, 72, 73, 74, 75, 76, 77, 80, 81, 82, 83, 84, 85, 86, 87, 88, 92 and 93.

What is claimed is:

1. A compound of formula (I):

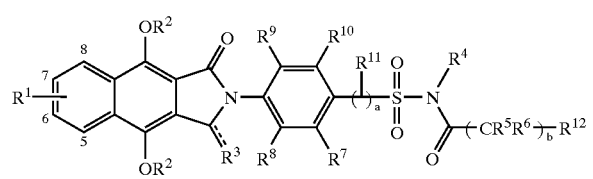

(I)

and pharmaceutically acceptable salt or solvate thereof wherein:
a=0 or 1;
b=0 to 3;
R$^1$ is selected from the group consisting of H, halogen, C$_{1-6}$aLkyl, S—C$_{1-6}$alkyl, C$_{1-6}$alkoxy, OCF$_3$, OCH$_2$CF$_3$, O-cyclopropyl, OCH$_2$-cyclopropyl, NH$_2$, NHC$_{1-6}$alkyl, N(C$_{1-6}$alkyl)$_2$, NO$_2$, OH, CH$_2$OC$_{1-6}$alkyl, and CH$_2$OH;
R$^2$ each independently is selected from C$_{1-4}$alkyl;
R$^3$ is H or O;
R$^4$ is H or C$_{1-6}$alkyl;
R$^5$ and R$^6$ each independently are selected from the group consisting of H, halogen, and C$_{1-3}$alkyl; or R$^5$ and R$^6$ are taken together to form a cyclopropyl ring;
R$^7$ to R$^{10}$ each independently are selected from the group consisting of H, C$_{1-6}$alkyl, C$_{1-6}$alkoxy, C$_{1-6}$alkoxy substituted by one or more fluorine atoms, O-cyclopropyl, OCH$_2$-cyclopropyl, S—C$_{1-6}$alkyl, NH$_2$, NHC$_{1-6}$alkyl, N(C$_{1-6}$alkyl)$_2$, halogen, NO$_2$, OH, CH$_2$OC$_{1-6}$alkyl, and CH$_2$OH;
R$^{11}$ is selected from the group consisting of H, OH, halogen, NH$_2$, NHC$_{1-6}$alkyl, N(C$_{1-6}$alkyl)$_2$, C$_{1-6}$alkyl, C$_{1-6}$alkoxy, NHCO(C$_{1-6}$alkyl), and =O;
R$^{12}$ is selected from the group consisting of H, C$_{1-6}$alkyl, phenyl, phenyl substituted by one or more R$^{13}$, phenyl fused to a heterocycle, naphthyl, naphthyl substituted by one or more R$^{13}$, C$_{4-7}$cycloalkyl, C$_{4-7}$cycloalkyl fused to a benzene ring, OCOC$_{1-6}$alkyl, heteroaryl, and heteroaryl substituted by one or more R$^{13}$;
R$^{13}$ is selected from the group consisting of halogen, C$_{1-6}$alkyl, C$_{1-6}$alkyl substituted by one or more fluorine atoms, C$_{1-6}$alkoxy, C$_{1-6}$alkoxy substituted by one or more fluorine atoms, phenyl, CN, CO$_2$H, CO$_2$C$_{1-6}$alkyl, OH, NH$_2$, NHC$_{1-6}$alkyl, N(C$_{1-6}$alkyl)$_2$, S(O)$_n$C$_{1-6}$alkyl wherein n is 0, 1 or 2, SO$_2$N(C$_{1-6}$alkyl)$_2$, CONH$_2$, CONHC$_{1-6}$alkyl CON(C$_{1-6}$alkyl)$_2$, COC$_{1-6}$alkyl, benzyloxy, CH$_2$CO$_2$H, CH$_2$CO$_2$C$_{1-6}$alkyl, NO$_2$, and NHCO(C$_{1-6}$alkyl); and
provided that:

----- R3 is a single bond or,
===== R3 is a carbonyl double bond, when R$^3$ is O.

2. The compound according to claim 1, wherein a=1.

3. The compound according to claim 1, wherein b=1.

4. The compound according to claim 1, wherein R$^1$ is H or bromine.

5. The compound according to claim 1, wherein each R$^2$ is ethyl.

6. The compound according to claim 1, wherein R$^4$ is H or methyl.

7. The compound claim 1, wherein R$^5$ and R$^6$ each independently are selected from the group consisting of H, chlorine, methyl, and ethyl; or R$^5$ and R$^6$ are taken together to form a cyclopropyl ring.

8. The compound according to claim 1, wherein each of R$^7$ to R$^{11}$ is H.

9. The compound according to claim 1, wherein R$^1$ is at the 6-position of the naphthalene ring, as claimed in formula (I).

10. The compound of formula (I) according to claim 1, wherein the compound is selected from the group consisting of:

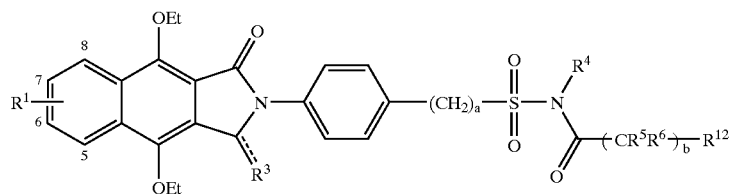

| Example | A | b | R¹ | R³ | R⁴ | R⁵ | R⁶ | R¹² |
|---|---|---|---|---|---|---|---|---|
| 1 | 1 | 1 | H | O | H | H | H | phenyl; |
| 2 | 1 | 1 | H | O | H | H | H | 4-methoxyphenyl; |
| 3 | 1 | 0 | H | O | H | — | — | 4-cyanophenyl; |
| 4 | 1 | 0 | H | O | H | — | — | Phenyl; |
| 5 | 1 | 0 | H | O | H | — | — | 3-fluorophenyl; |
| 6 | 1 | 0 | H | O | H | — | — | 4-nitrophenyl; |
| 7 | 1 | 0 | H | O | H | — | — | 4-fluorophenyl; |
| 8 | 1 | 0 | H | O | H | — | — | Methyl; |
| 9 | 1 | 0 | H | O | H | — | — | n-butyl; |
| 10 | 1 | 0 | H | O | H | — | — | t-butyl; |
| 11 | 1 | 0 | H | O | H | — | — | Cyclohexyl; |
| 12 | 1 | 1 | H | O | H | H | H | OC(O)CH₃; |
| 13 | 1 | 0 | H | O | — | — | — | Napth-2-yl; |
| 14 | 1 | 0 | H | O | — | — | — | 5-methyl-1,2-oxazol-5-yl; |
| 15 | 1 | 2 | H | O | H | H | H | Phenyl; |
| 16 | 1 | 2 | H | O | H | H | H | Cyclohexyl; |
| 17 | 1 | 0 | H | O | H | — | — | furan-2-yl; |
| 18 | 1 | 1 | H | H | H | H | H | phenyl; |
| 19 | 1 | 1 | H | H | H | H | H | 3,4-dichlorophenyl; |
| 20 | 1 | 1 | H | H | H | H | H | 4-methylphenyl; |
| 21 | 1 | 1 | H | H | H | H | H | 2-methylphenyl; |
| 22 | 1 | 1 | H | H | H | Me | Me | Phenyl; |
| 23 | 1 | 1 | H | H | H | H | H | 4-i-butylphenyl; |
| 24 | 1 | 1 | H | H | H | H | H | 4-methoxyphenyl; |
| 25 | 1 | 1 | H | H | H | H | H | 3-fluorophenyl; |
| 26 | 1 | 1 | H | H | H | H | H | 3-methylphenyl; |
| 27 | 1 | 1 | H | H | H | H | H | 4-i-propylphenyl; |
| 28 | 1 | 1 | H | H | H | H | H | 4-ethylphenyl; |
| 29 | 1 | 1 | H | H | H | H | H | 2-chlorophenyl; |
| 30 | 1 | 1 | H | H | H | H | H | 4-phenylphenyl; |
| 31 | 1 | 1 | H | H | H | H | H | 2-methoxyphenyl; |
| 32 | 1 | 1 | H | H | H | H | H | 2-fluorophenyl; |
| 33 | 1 | 1 | H | H | H | H | H | 4-trifluoro methylphenyl; |
| 34 | 1 | 1 | H | H | H | H | H | 2,3-dimethoxy phenyl; |
| 35 | 1 | 1 | H | H | H | H | H | 4-hydroxyphenyl; |
| 36 | 1 | 1 | H | H | H | H | H | 2,5-dimethoxy phenyl; |
| 37 | 1 | 1 | H | H | H | H | H | 4-dimethylamino phenyl; |
| 38 | 1 | 1 | H | H | H | H | H | 3,4-dimethoxy phenyl; |
| 39 | 1 | 1 | H | H | H | H | H | 2,5-dimethylphenyl; |
| 40 | 1 | 1 | H | H | H | Me | H | 4-i-butylphenyl; |
| 41 | 1 | 1 | H | H | H | H | H | 2-benzyloxyphenyl; |
| 42 | 1 | 1 | H | H | H | H | H | 3-benzyloxyphenyl; |
| 43 | 1 | 1 | H | H | H | H | H | 3-methoxyphenyl; |
| 44 | 1 | 1 | H | H | H | H | H | 2-(CH₂CO₂H)phenyl; |
| 45 | 1 | 1 | H | H | H | H | H | 4-(CO₂Me)phenyl; |
| 46 | 1 | 1 | H | H | H | H | H | 4-(SO₂NMe₂) phenyl; |
| 47 | 1 | 1 | H | H | H | H | H | 2-(CH₂CO₂Me) phenyl; |
| 48 | 1 | 1 | H | H | H | H | H | naphth-2-yl; |
| 49 | 1 | 0 | H | H | H | — | — | ![bicyclic structure] |
| 50 | 1 | 1 | H | H | H | Cyclopropyl | | phenyl; |
| 51 | 1 | 1 | H | H | H | H | H | thiophen-3-yl; |
| 52 | 1 | 1 | H | H | H | H | H | pyridin-3-yl; |
| 53 | 1 | 1 | H | H | H | H | H | thiophen-2-yl; |
| 54 | 1 | 1 | H | H | H | H | H | pyridin-2-yl; |
| 55 | 1 | 1 | H | H | H | H | H | pyridin-4-yl; |
| 56 | 1 | 1 | H | H | H | H | H | 2-methyl-1,3-thiazol-4-yl; |
| 57 | 1 | 1 | H | H | H | H | H | 4-methyl-1,2,5-oxadiazol-3-yl; |
| 58 | 1 | 1 | H | H | H | H | H | 5-methyl-1,2-oxazol-3-yl; |
| 59 | 1 | 1 | H | H | H | H | H | 3-methyl-1,2-oxazol-5-yl; |
| 60 | 1 | 1 | H | H | H | H | H | 4-methyl-1,3-thiazol-5-yl; |
| 61 | 1 | 1 | H | O | H | H | H | 2-methylphenyl; |

-continued

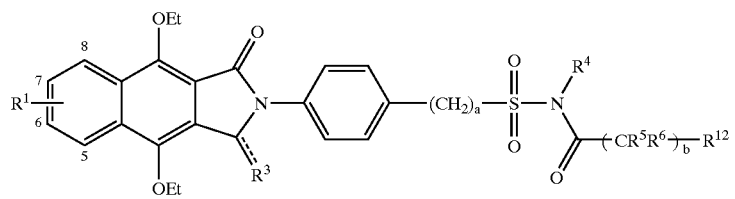

| Example | A | b | R¹ | R³ | R⁴ | R⁵ | R⁶ | R¹² |
|---|---|---|---|---|---|---|---|---|
| 62 | 1 | 1 | H | O | H | H | H | 4-fluorophenyl; |
| 63 | 1 | 1 | H | O | H | H | H | 3-methoxyphenyl; |
| 64 | 1 | 1 | H | O | H | Et | H | Phenyl; |
| 65 | 1 | 1 | H | O | H | H | H | 3-fluorophenyl; |
| 66 | 1 | 1 | H | O | H | H | H | 3,4-dimethoxy phenyl; |
| 67 | 1 | 1 | H | O | H | H | H | 4-methylphenyl; |
| 68 | 1 | 1 | H | O | H | Me | H | Phenyl; |
| 69 | 1 | 1 | H | O | H | H | H | 2,5-difluorophenyl; |
| 70 | 1 | 1 | H | O | H | H | H | 4-chlorophenyl; |
| 71 | 1 | 1 | H | O | H | H | H | 2-methoxyphenyl; |
| 72 | 1 | 1 | H | O | H | H | H | 2,6-dimethylphenyl; |
| 73 | 1 | 1 | H | O | H | Me | Me | 3-methylphenyl; |
| 74 | 1 | 1 | H | O | H | H | H | 3-fluoro-4-methylphenyl; |
| 75 | 1 | 1 | H | O | H | Cl | H | phenyl; |
| 76 | 1 | 1 | H | O | H | H | H | naphth-1-yl; |
| 77 | 1 | 1 | H | O | H | H | H | naphth-2-yl; |
| 78 | 0 | 0 | H | O | H | — | — | Methyl; |
| 79 | 1 | 1 | H | H | H | H | H | 4-methyl-1,3-thiazol-5-yl; |
| 80 | 1 | 1 | H | H | H | H | H | 4-trifluoromethoxyphenyl; |
| 81 | 1 | 1 | H | H | H | H | H | 3-trifluoromethoxyphenyl; |
| 82 | 1 | 1 | H | H | H | H | H | 3,4-diethoxyphenyl; |
| 83 | 1 | 1 | H | H | H | H | H | 3,5-dimethoxy phenyl; |
| 84 | 1 | 1 | H | H | H | H | H | benzo[1,3]dioxol-5-yl; |
| 85 | 1 | 1 | H | H | H | H | H | 2,2-dimethyl-benzo[1,3]dioxol-5-yl; |
| 86 | 1 | 1 | H | H | H | Me | H | 6-methoxy-naphth-2-yl; |
| 87 | 1 | 1 | H | H | H | H | H | 1-methylindol-3-yl; |
| 88 | 1 | 1 | H | H | H | H | H | 4-methylbenzofuran-3-yl; |
| 89 | 1 | 1 | H | H | H | H | H | 1,3-dimethylindol-2-yl; |
| 90 | 1 | 1 | H | H | H | H | H | 2-methylbenzofuran-3-yl; |

-continued

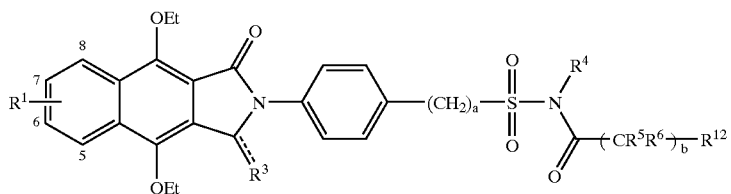

| Example | A | b | R¹ | R³ | R⁴ | R⁵ | R⁶ | R¹² |
|---|---|---|---|---|---|---|---|---|
| 91 | 1 | 0 | H | H | H | — | — | |
| 92 | 1 | 0 | H | H | H | — | — | |
| 93 | 1 | 1 | H | O | H | H | H | | and

| 94 | 1 | 1 | H | H | CH₃ | H | H | 4-methoxyphenyl. |

11. A process for preparation of compound(s) of formula (I) and pharmaceutically acceptable salt or solvate thereof as claimed in claim 1, which comprises:

(A) coupling a sulfonamide of formula (II):

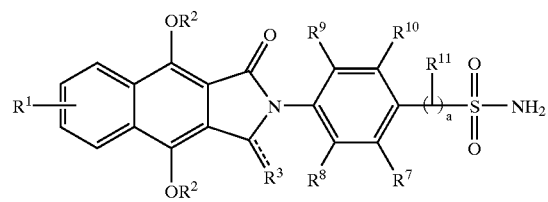

(II)

or a protected derivative thereof with an acid chloride of formula (Iii):

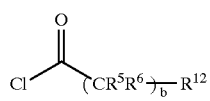

(III)

or a protected derivative thereof; or (B) coupling a sulfonamide of formula (II):

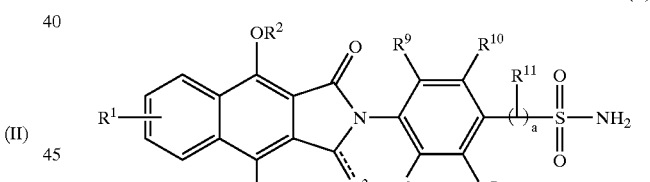

(II)

or a protected derivative thereof with an acid of formula (IV):

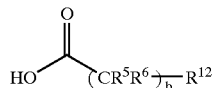

(IV)

or a protected derivative thereof; or (C) interconverting a compound of formula (I) into another compound of formula (I); or (D) deprotecting a protected derivative of compound of formula (I); and optionally converting compounds of formula (I) prepared by any one of processes or process steps (A) to (D) into pharmaceutically acceptable salt or solvate thereof.

12. A pharmaceutical compositions comprising a compound of formula (I) or a pharmaceutically acceptable salt or solvate thereof as claimed in claim 1 in admixture with one or more physiologically acceptable carriers or excipients.

13. A method of treating a human or animal subject suffering from a condition which is mediated by the action of $PGE_2$ at EP4 receptors, wherein said method comprises administering to said subject an effective amount of a compound of formula (I) or a pharmaceutically acceptable salt or solvate thereof as claimed in claim 1; and wherein said condition is selected from the group consisting of rheumatoid arthritis, osteoarthritis, rheumatoid spondylitis, qouty arthritis, musculoskeletal pain, lower back and neck pain, sprains and strains, neuropathic pain, sympathetically maintained pain, myositis, pain associated with cancer and fibromyalgia, pain associated with migraine, pain associated with influenza or other viral infections, rheumatic fever, pain associated with functional bowel disorders, non-cardiac chest pain, pain associated with myocardial ischemia, post operative pain, headache, toothache, dysmenorrheal, inflammation, osteoporosis, neurodegenerative diseases, kidney and gastrointestinal dysfunction.

* * * * *